BEST AVAILABLE COPY
Aug 7, 1951 E. S. BOERNER Plant Pat. 1,025
ROSE PLANT
Filed May 29, 1950
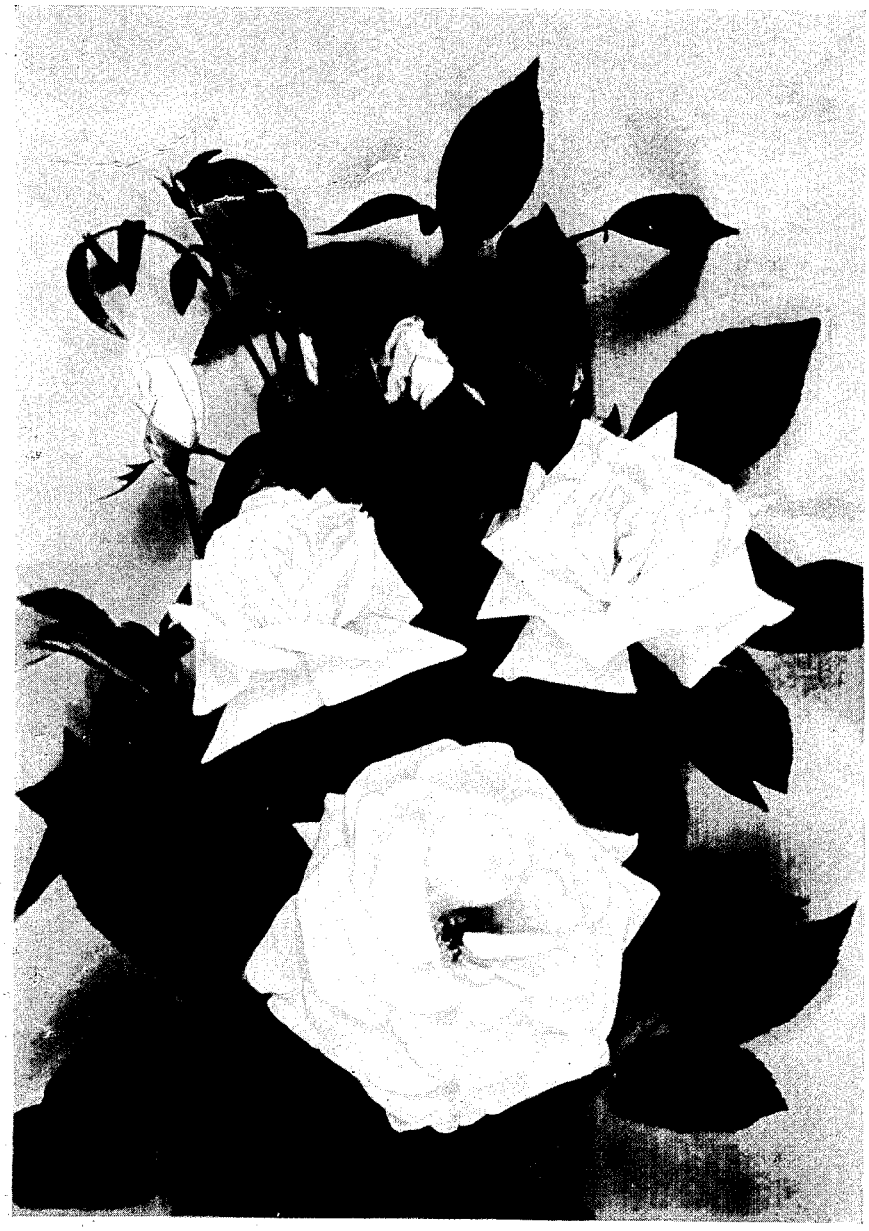
Inventor.
E. S. Boerner
By: Robert Cobb
Attorneys.

Patented Aug. 7, 1951

Plant Pat. 1,025

BEST AVAILABLE COPY

UNITED STATES PATENT OFFICE 1,025

ROSE PLANT

Eugene S. Boerner, Newark, N. Y., assignor to Jackson & Perkins Company, Newark, N. Y., a corporation of New York Application May 29, 1950, Serial No. 164,897

1 Claim. (Cl. 47—61)

The present invention relates to a new and distinct variety of rose plant of the large-flowered polyantha class, originated by crossing an unnamed and unpatented white colored hybrid tea variety with the variety "Summer Snow" (Plant Patent No. 416), which latter parent is notable for its large white flowers borne in large clusters, and by its continuously recurrent blooming habit.

The general objective in making this cross was to obtain a white rose which would be suitable for both greenhouse and outdoor use. This objective was satisfactorily attained.

This new variety is still further distinguished from its parents, as well as from other varieties, by the following dominant characteristics:

(1) The shape and color of the blooms, which are entirely different from any other variety now in commerce;

(2) The Forest Green shade of color of the foliage which is an effective foil for the white blooms; and (3) The long-lasting quality of the blooms, which makes this new variety very effective as an outdoor plant, as a pot plant, and also as a greenhouse cut flower.

Asexual reproduction of the new variety by budding at Newark, New York, and at Pleasanton, California, shows that the foregoing characteristics come true to form and are established and transmitted through succeeding propagations.

The accompanying drawing shows specimens of the new variety, with the flowers and foliage in different stages of development.

The following is a detailed description of the new variety, with color terminology in accordance with Ridgway's Color Standards and nomenclature:

Parentage: Seedling.

*Seed parent.*—Unnamed white hybrid tea.

*Pollen parent.*—"Summer Snow."

Classification:

*Botanic.*—Large-flowered polyantha.

*Commercial.*—Floribunda.

*Flower*

(Observations made in greenhouses at Newark, New York in the month of April, 1950.)

Blooming habit: Recurrent—continuous.

Bud:

*Size.*—Medium.

*Form.*—Ovoid. Is not affected by wet or hot weather.

*Color.*—When sepals first divide—Pale Green-Yellow, Plate 5. When petals begin to unfurl—Marguerite Yellow, Plate 30. When half blown—inside of petals: Marguerite Yellow, Plate 30; reverse of petals: White, Plate 53, lightly overcast with Marguerite Yellow, Plate 30.

*Sepals.*—Branched. Curl back when petals begin to unfurl. Color—inside: Turtle Green, Plate 32; outside: Biscay Green, Plate 17.

*Calyx.*—Shape—pear. Size—small. Aspect—smooth. Odor when rubbed—none. Color—Biscay Green, Plate 17.

*Peduncle.*—Length—medium. Aspect—rough. Color—Bice Green, Plate 17. Strength—erect; heavy.

*Opening.*—Bud opens up well. Is not affected by adverse weather conditions.

Bloom:

*Size.*—Large. Average size when fully expanded, 4½ inches.

*Borne.*—Singly, and several together.

*Stems.*—Medium; strong.

*Form.*—When first open—cupped. Permanence—retains its form to the end.

*Petalage.*—Double (full but open center). Number of petals under normal conditions, 25–30.

*Color.*—Center of flower—White, Plate 53, with slight overcast of Marguerite Yellow, Plate 30. Outer petals—White, Plate 53. Base of petals—Barium Yellow, Plate 16. Inside of petals—White, Plate 53, with slight overcast of Marguerite Yellow, Plate 30, extending from base of each petal to about center of petal. Reverse of petals—White, Plate 53, with slight overcast of Marguerite Yellow, Plate 30, extending from base of each petal to about center of petal. General tonality from a distance—White, Plate 53.

*Discoloration.*—General tonality at end of first day—White, Plate 53, with slight overcast of Ma[illegible], Plate 30. Second day—[illegible]ith slight overcast of Ma[illegible] Plate 30. Third day—White, [illegible]

Petals:

*Texture.*—Thick. Are not affected by wet or hot weather.

*Appearance.*—Inside—satiny. Outside—shiny.

*Form.*—Oval; slightly notched.

*Arrangement.*—Informal (with "rags" in center). Pentaloids in center—few and large.

BEST AVAILABLE COPY

*Persistence.*—Drop off cleanly.
*Fragrance.*—Slight. Nature—tea (average hybrid tea scent).
*Lasting quality.*—On the plant—long. As cut flower—long.

Genital organs:
*Stamens, anthers.*—Medium; many. Color—Apricot Yellow, Plate 4. Arrangement—regular around styles.
*Stamens, filaments (threads).*—Medium. Color—Martius Yellow, Plate 4.
*Pollen.*—Color—Maize Yellow, Plate 4.
*Styles.*—Bunched, of uneven length. Short, thin.
*Stigmas.*—Color—Sulphur Yellow, Plate 5.
*Ovaries.*—All enclosed in calyx.

*Plant*

Form: Bush.
Growth: Vigorous and upright.
Foliage: 5 to 7 leaflets.
*Size.*—Medium.
*Quantity.*—Normal.
*Color.*—New foliage—upper side — Forest Green, Plate 17; under side—Light Elm Green, Plate 17. Old foliage—upper side—Oil Green, Plate 5. Serrations—Oxblood Red, Plate 1. Under side—Yellowish Oil Green, Plate 5, lightly overcast with Oxblood Red, Plate 1. Serrations—Oxblood Red, Plate 1.
*Shape.*—Oval pointed.
*Texture.*—Upper side—glossy. Under side—smooth. Ribs and veins—ordinary.
*Edge.*—Serrated (saw toothed).

*Serrations.*—Single; small.
*Leaf stem.*—Color—Biscay Green, Plate 17. Under side—prickles.
*Stipules.*—Medium; bearded.
*Disease resistance.*—Resistant.

Wood:
*New wood.*—Color—Yellowish Oil Green, Plate 5. Bark—smooth. *Old wood.*—Color—Cress Green, Plate 31. Bark—smooth.

Thorns:
*Thorns.*—Quantity on main stalks from base and on laterals from stalk—ordinary. Form—narrow base. Medium length; hooked downward. Color when young—Carmine, Plate 1. Position—irregular.
*Prickles.*—Quantity on main stalks and on laterals—few. Color—Eugenia Red, Plate 13.
*Short needles.*—Quantity on main stalks and on laterals—none.

I claim:

A new distinct variety of rose plant of the large-flowered polyantha class, characterized as to novelty by the unique shape and color of its blooms, by the Forest Green shade of color of its foliage which forms an effective foil for the blooms, and by the long-lasting quality of its blooms which makes it very effective as an outdoor plant, as a pot plant, and as a cut flower in the greenhouse, substantially as shown and described.

EUGENE S. BOERNER.

No references cited.